(12) United States Patent
Wetzel et al.

(10) Patent No.: US 9,808,797 B2
(45) Date of Patent: Nov. 7, 2017

(54) RESISTANCE ANALYTICAL FURNACE

(71) Applicant: Leco Corporation, St. Joseph, MI (US)

(72) Inventors: Joshua N. Wetzel, Benton Harbor, MI (US); Gordon C. Ford, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 1173 days.

(21) Appl. No.: 13/920,575

(22) Filed: Jun. 18, 2013

(65) Prior Publication Data
US 2013/0334198 A1   Dec. 19, 2013

Related U.S. Application Data (60) Provisional application No. 61/661,595, filed on Jun. 19, 2012.

(51) Int. Cl.
*B01L 3/04* (2006.01)
*G01N 31/12* (2006.01)

(52) U.S. Cl.
CPC ................ *B01L 3/04* (2013.01); *G01N 31/12* (2013.01)

(58) Field of Classification Search
CPC .................................. G01N 31/12; B01L 3/04
USPC ........ 219/426, 427, 531, 119, 120; 373/118, 373/109, 113, 117
See application file for complete search history.

(56) References Cited

U.S. PATENT DOCUMENTS

| | | | |
|---|---|---|---|
| 2,903,495 A * | 9/1959 | Dickson | C22B 34/1295 164/495 |
| 3,139,474 A | 6/1964 | Weech | |
| 3,619,839 A | 11/1971 | Kraus et al. | |
| 3,636,229 A | 1/1972 | Sitek et al. | |
| 3,751,965 A | 8/1973 | Kraus | |
| 3,812,705 A | 5/1974 | Boillot | |
| 3,899,627 A | 8/1975 | Sitek et al. | |
| 3,936,587 A * | 2/1976 | Sitek | F27B 17/02 219/426 |
| 4,056,677 A | 11/1977 | Berk et al. | |
| 4,072,814 A | 2/1978 | Boillot | |
| 4,328,386 A | 5/1982 | Bredeweg | |

(Continued)

FOREIGN PATENT DOCUMENTS

JP    04273986 A  *  9/1992

OTHER PUBLICATIONS

1 page showing five of Applicant's commercially available prior art crucibles.

*Primary Examiner* — Dana Ross
*Assistant Examiner* — Kuangyue Chen
(74) *Attorney, Agent, or Firm* — Price Heneveld LLP (57) ABSTRACT

A resistance furnace provides an improved upper and lower electrode construction with significantly increased coolant flow. The lower electrode has a tip design that significantly lowers the electrode tip temperature during an analysis. The upper and lower electrodes also cooperate with an improved crucible design to significantly reduce the power required to fuse a specimen contained in the crucible. The furnace uniformly heats the floor and lower side walls of a crucible, which lowers the power requirement for specimen fusion and provides higher structural benefits to provide consistent analysis and manufacturing yields. The crucible has a cylindrical body and pedestal base with an annular smoothly curved concave indentation therebetween.

4 Claims, 12 Drawing Sheets

(56) References Cited

U.S. PATENT DOCUMENTS

| | | | |
|---|---|---|---|
| 4,419,754 A * | 12/1983 | Sitek | H05B 3/08 |
| | | | 219/427 |
| 4,728,769 A * | 3/1988 | Nishiwaki | B23K 35/0205 |
| | | | 219/119 |
| 5,452,881 A * | 9/1995 | Hayashi | B01L 3/04 |
| | | | 266/245 |
| 6,200,385 B1 * | 3/2001 | Swinehart | C30B 11/00 |
| | | | 117/220 |
| 6,270,727 B1 | 8/2001 | Mitchell et al. | |
| 6,291,802 B1 | 9/2001 | Ford | |
| 7,402,280 B2 | 7/2008 | Ford | |
| 2012/0213244 A1 | 8/2012 | Latino et al. | |
| 2012/0213678 A1 | 8/2012 | Ford | |

\* cited by examiner

RESISTANCE ANALYTICAL FURNACE

CROSS-REFERENCE TO RELATED APPLICATIONS

This application claims priority under 35 U.S.C. §119(e) and the benefit of U.S. Provisional Application No. 61/661,595 entitled RESISTANCE ANALYTICAL FURNACE, filed on Jun. 19, 2012, by Joshua N. Wetzel, et al., the entire disclosure of which is incorporated herein by reference.

BACKGROUND OF THE INVENTION

The present invention relates to analytical furnaces and particularly to an improved electrode structure of a resistance furnace and the combination of the electrode structure with a resistance crucible.

Analytical furnaces heat specimens, such as chips and pin samples, and the like, typically ranging in mass from about 1 mg to about 1 gram in a resistive crucible, typically made of graphite. Resistance furnaces employ such graphite crucibles which are clamped between two electrodes to pass an electrical current through the crucible, heating specimens to temperatures of 2500° C.-3000° C. or higher. The gaseous byproducts of fusing the specimen are then swept by an inert gas, such as helium, through the furnace system to an analyzer for the subsequent analysis of the specimen gases of interest using suitable detectors. Such an analyzer is represented by Model ONH836, which is commercially available from Leco Corporation of St. Joseph, Mich.

The heating of a specimen in existing graphite crucibles requires a significant amount of electrical power, in the neighborhood of 7500 watts. This, in turn, requires the electrodes coupled to the graphite crucible to be water cooled. Even with water cooling and the use of tungsten/copper alloy tipped electrodes, the electrodes tend to wear. The use of replaceable tips, such as disclosed in U.S. Pat. No. 4,419,754, although protecting the body of the electrode, still require frequent replacement since, even though water cooled, the electrode tips can be subjected to temperatures as high as 1050° C. during use. Also, existing crucible geometries, such as represented by U.S. Pat. Nos. 3,636,229, 3,899,627, and 4,328,386, when heated to temperatures approaching or exceeding 3000° C., tend to have hot spots instead of uniformly heated floors. Also, their side walls allow a specimen, which is heated to a bubbling state, to overflow the crucible and, in some cases, contaminate the upper electrode.

There exists a need, therefore, to improve the performance of existing resistance furnaces, including reducing power consumption, improving electrode lifetime, and providing a crucible which, when used with the electrodes, fuses a variety of specimen shapes efficiently without contaminating the upper electrode.

SUMMARY OF THE INVENTION

The furnace of this invention provides an improved electrode construction with coolant flow and an electrode tip design that significantly lowers the tip temperature during an analysis, thereby greatly increasing the life of the tipped electrodes resulting in increased cycles of use before requiring replacement. The electrodes also cooperate with an improved crucible design to significantly reduce the power required to fuse a specimen contained in the crucible. The furnace uniformly heats the floor and lower side walls of a crucible, which is designed to enable a lower power requirement for specimen fusion and higher structural benefits to improve consistent analysis and manufacturing yields.

An electrode assembly for a resistance furnace of this invention includes a generally cylindrical upper electrode including a central axially extending aperture for admission of a sample into a crucible held within the electrodes in an enlarged cylindrical furnace area. The upper electrode includes a generally funnel-shaped lower end for receiving the crucible-holding pedestal of a lower electrode. The lower electrode has a pedestal for supporting a crucible and is shaped to be raised into sealable engagement within the funnel-shaped lower end of the upper electrode. The lower electrode includes a generally truncated conical recess formed in the bottom of the pedestal and a cooling water inlet and a cooling water outlet communicating with the conical recess. A nozzle is positioned in the conical recess of the lower electrode and has a discharge end closely positioned with respect to the interior wall of the truncated conical recess. The nozzle is coupled to the water inlet for projecting cooling water toward the pedestal of the lower electrode.

When such electrodes are combined with the use of a graphite crucible having a cylindrical body with a pedestal base with an inwardly extending concave annular indentation between the body and the base, the resultant furnace operation is highly efficient. Also, the electrodes have a greatly improved lifecycle before requiring replacement.

These and other features, objects and advantages of the present invention will become apparent upon reading the following description thereof together with reference to the accompanying drawings.

DETAILED DESCRIPTION OF THE PREFERRED EMBODIMENT

Figure 1:
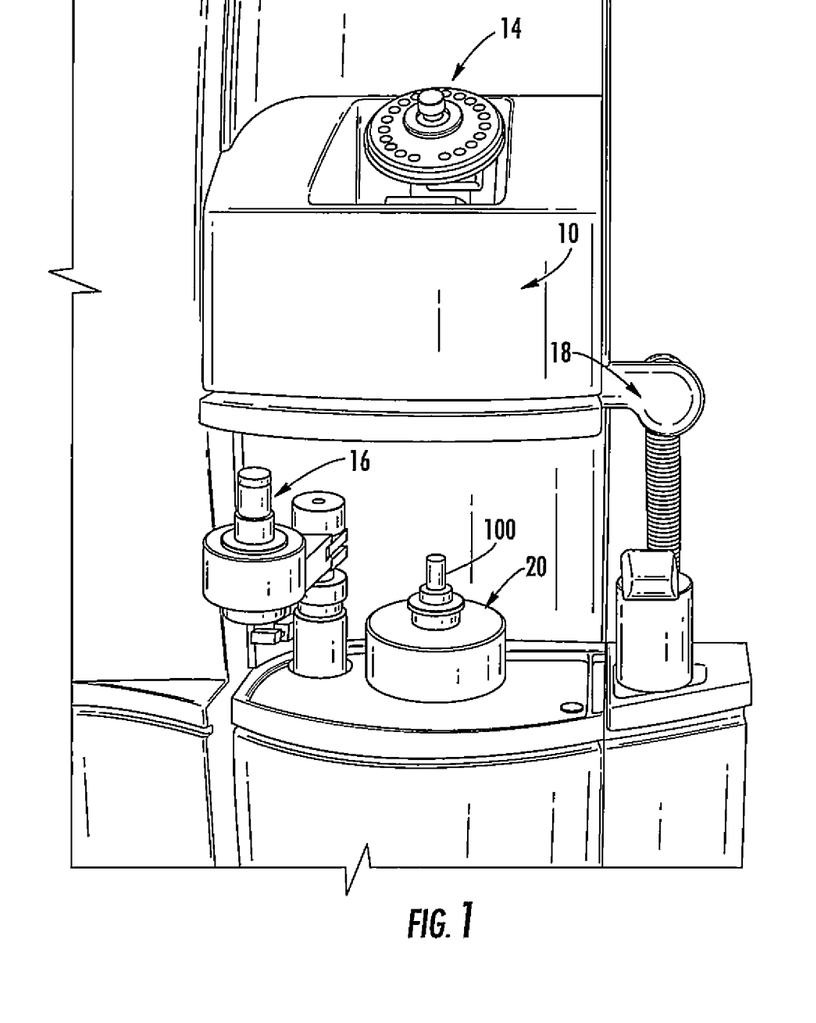
FIG. 1 is a fragmentary perspective view of an analyzer including a furnace which includes the electrode assembly of the present invention.
Figure 2:
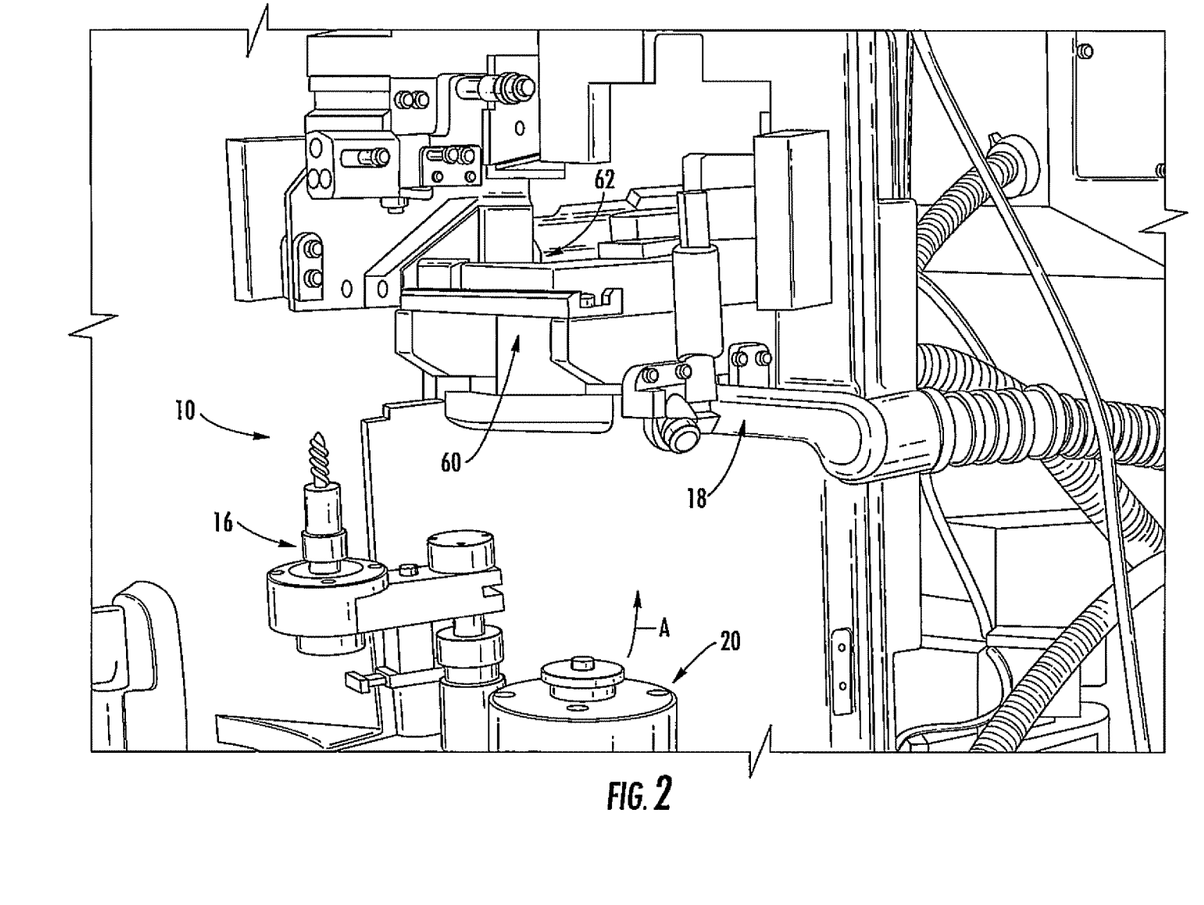
FIG. 2 is an enlarged perspective view of the analyzer shown in FIG. 1, shown with the cabinet cover removed to expose the furnace area and sample drop mechanism.
Figure 3:
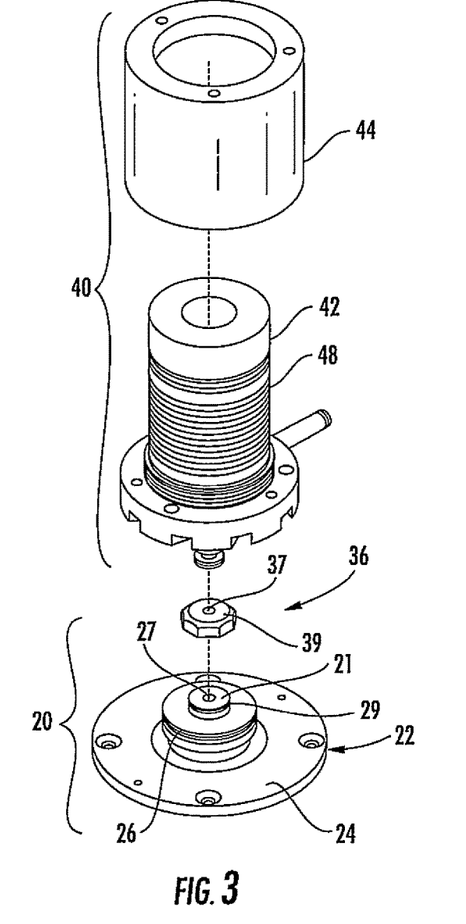
FIG. 3 is an exploded perspective view of the electrode assembly used in the furnace.
Figure 4:
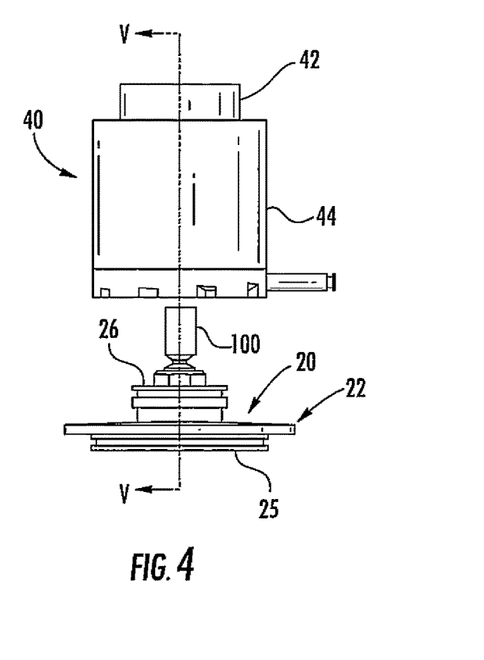
FIG. 4 is a front elevational exploded view of the upper and lower electrodes in an open position and shown with a crucible positioned on the lower electrode.

Referring initially to FIGS. 1 and 2, there is shown an oxygen/nitrogen/hydrogen analyzer 10, such as a model OHN836 commercially available from Leco Corporation of St. Joseph, Mich., but modified to include the present invention. The analyzer includes a touch screen control (not shown) for the operation of the furnace and components of the analyzer and an inclined sample loading carousel 14 of the type described in pending patent application Ser. No. 13/402,192, entitled SAMPLE LOADING CAROUSEL, which was filed on Feb. 22, 2012. The analyzer also includes an electrode power cleaning brush assembly 16 together with a vacuum cleaning mechanism 18 of the type described in U.S. patent application Ser. No. 13/358,096 entitled VACUUM CLEANING STRUCTURE FOR ELECTRODE FURNACE, which was filed on Jan. 25, 2012. The disclosures of both of these applications are incorporated herein by reference.

As seen in FIGS. 1 and 2, the analyzer 10 includes a lower electrode assembly 20 which includes a pedestal as described below for receiving a crucible 100 (FIGS. 1, 4, 5 and 7-15). The lower electrode assembly 20 can be raised in a direction indicated by arrow A in FIGS. 2 and 5 to insert a crucible positioned on the lower electrode into the furnace area 60 in the upper electrode assembly 40 (FIGS. 3-7).

Figure 5:
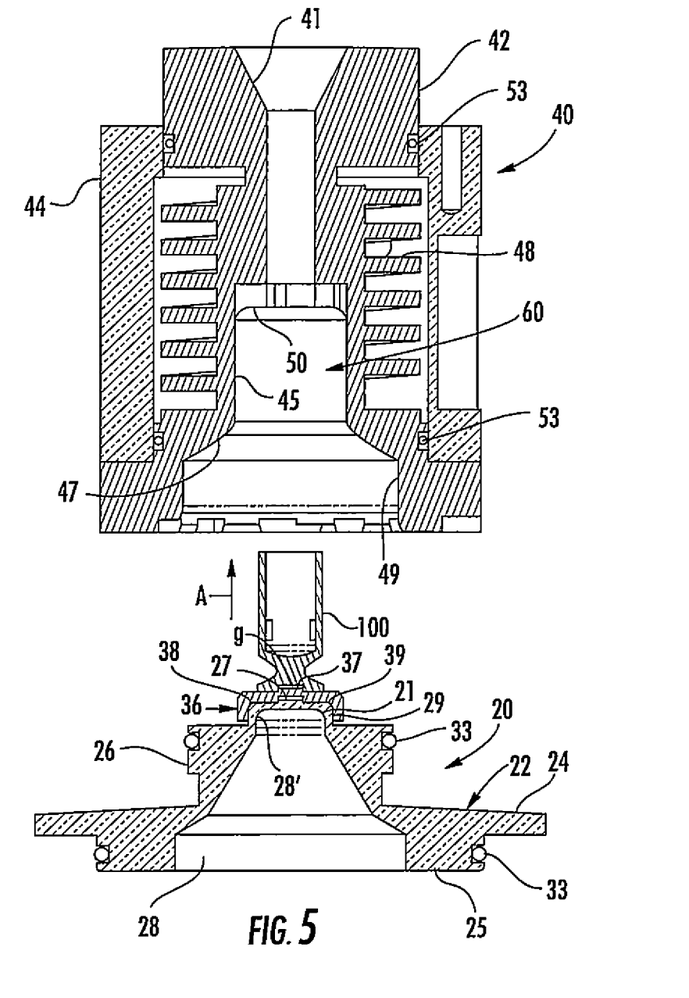
FIG. 5 is an enlarged cross-sectional view of the structure shown in FIG. 4, taken along section lines V-V of FIG. 4.
Figures 6, 7:
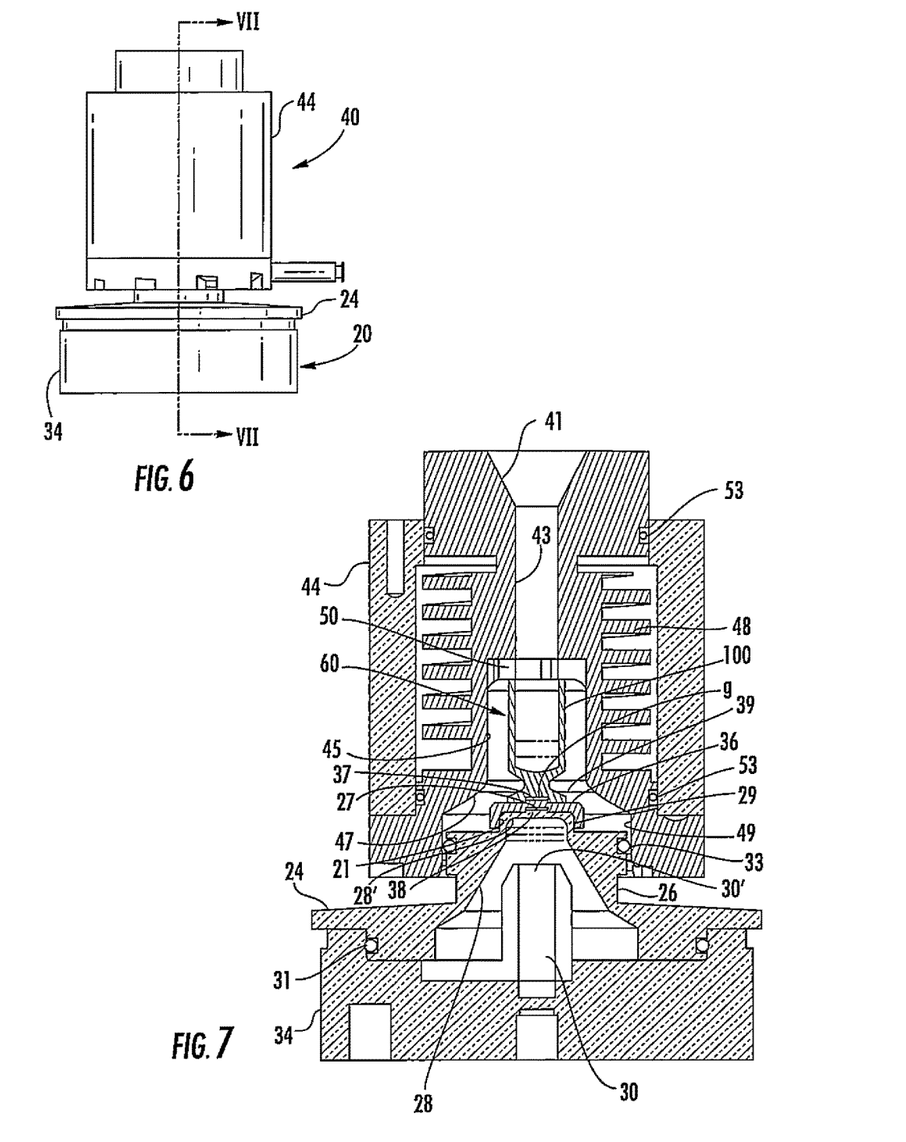
FIG. 6 is a front elevational view of the electrode assembly shown in a closed position.
FIG. 7 is an enlarged cross-sectional view, taken along section line VII-VII in FIG. 6, showing the components of the furnace including the positioning of a crucible therein.

As seen in FIGS. 3-7, the electrode structure for the furnace 60 comprises a lower electrode assembly 20 and an upper electrode assembly 40, both of which are water cooled. The lower electrode assembly 20 includes a lower electrode 22 made of copper and having a generally disk-shaped center body 24 and an upwardly projecting pedestal 26. The electrode 22 includes a downwardly extending annular section 25. The bottom of electrode 22 includes an upwardly extending truncated conical recess 28 which terminates in a cylindrical upper end section 28' (FIGS. 5 and 7). The top wall of section 28' is relatively thin (0.050-0.080 inch) to provide heat transfer from the alloy tip 36 threaded onto projection 21. Recess 28 houses a water projecting nozzle 30 (FIGS. 7-9) which is coupled to the cooling water inlet 32 (FIG. 8) in the water jacket 34 (FIGS. 6 and 7) surrounding the lower annular section 25 of electrode 22. The discharge upper end of nozzle 30 is closely spaced (0.45 inches) from the top wall of section 28'. The enlarged flared lower end of truncated conical recess 28 of the lower electrode 22 provides a significant internal surface area and volume to allow a significant cooling water flow rate of from about 0.95 to 1.05 gallons per minute (gpm) to cool the lower electrode 20 during an analysis.

Lower electrode 22 includes an upwardly extending circular projection 21 (FIG. 3) on the top center of pedestal 26, which has external peripheral threads 29 (FIG. 7) to receive a cup-shaped tungsten/copper alloy (10% Cu, 90% W) tip 36, which is internally threaded to screw onto center circular projection 21 when assembled, as seen in FIGS. 5 and 7-9. The facing surfaces of tip 36 and projection 21 are machined flat (i.e., to a geometric tolerance of 0.002 inch) to provide maximum electrical contact between the tip 36 and the electrode 22. The inside of the cup-shaped tip 36 includes a circular recess 38 in which a button-like projection 27 (FIG. 3) on the tip-receiving projection 21 extends. The tip 36 includes a centered upwardly projecting button 37 which, as seen in FIGS. 5 and 7-9, extends into an indentation 124 (FIGS. 13 and 15) in the bottom of the pedestal 114 of crucible 100. The button 37 has a height less than the depth of the indentation 124 in the bottom of pedestal 114 to leave a gap "g" (FIG. 9) between the upper surface of button 37 and the floor 125 of the recess in pedestal 114 of about 0.020 inches. The only contact between the tip 36 and the pedestal 114 of crucible 100 is the annular area 39 (FIGS. 3 and 5) of tip 36 surrounding button 37, and the annular bottom surface 132 (FIGS. 13-15) of the crucible.

Figure 8:
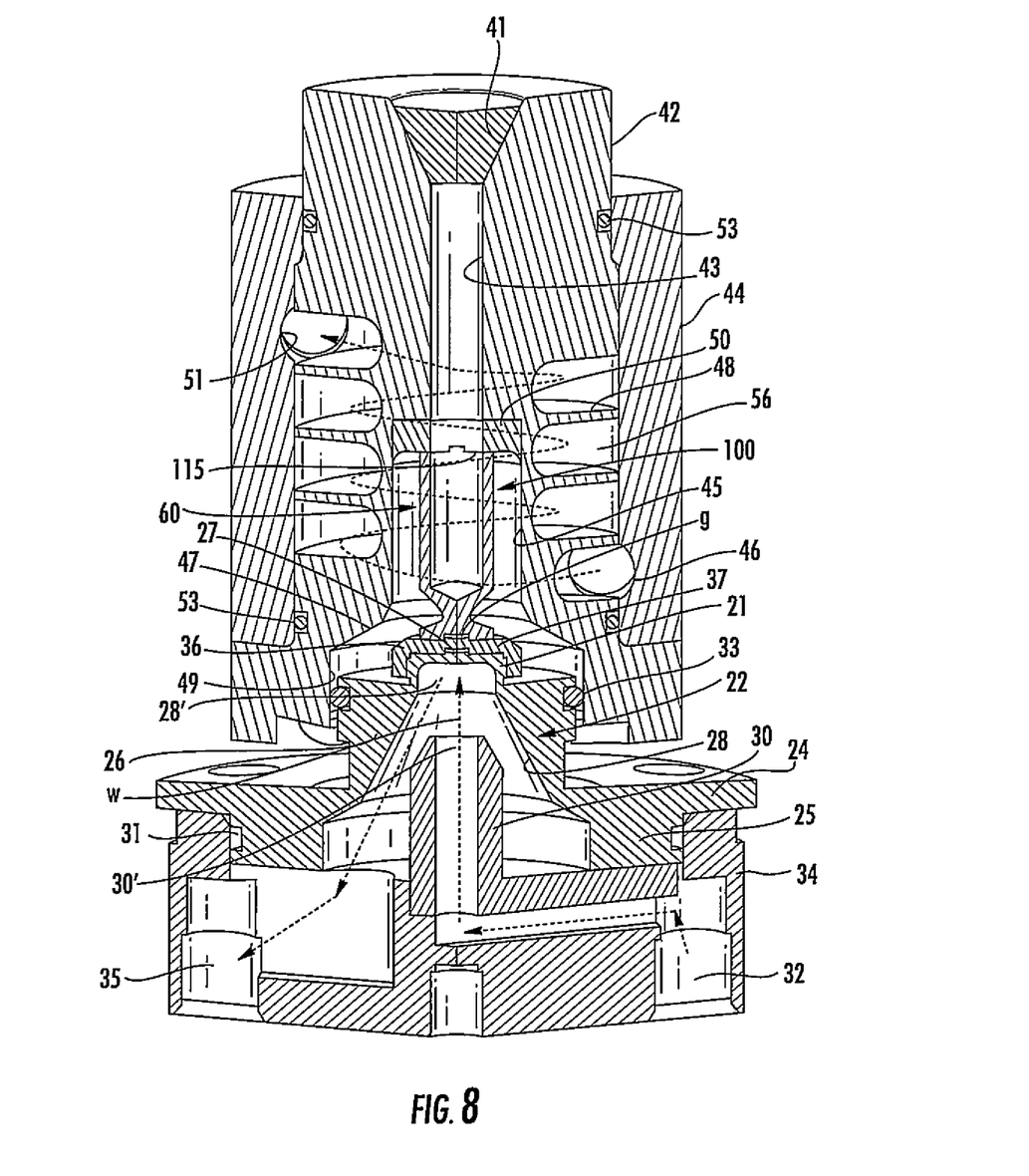
FIG. 8 is a pictorial cross-sectional view of the structure shown in FIG. 7, illustrating in dotted lines the water flow path for cooling the upper and lower electrodes.
Figure 9:
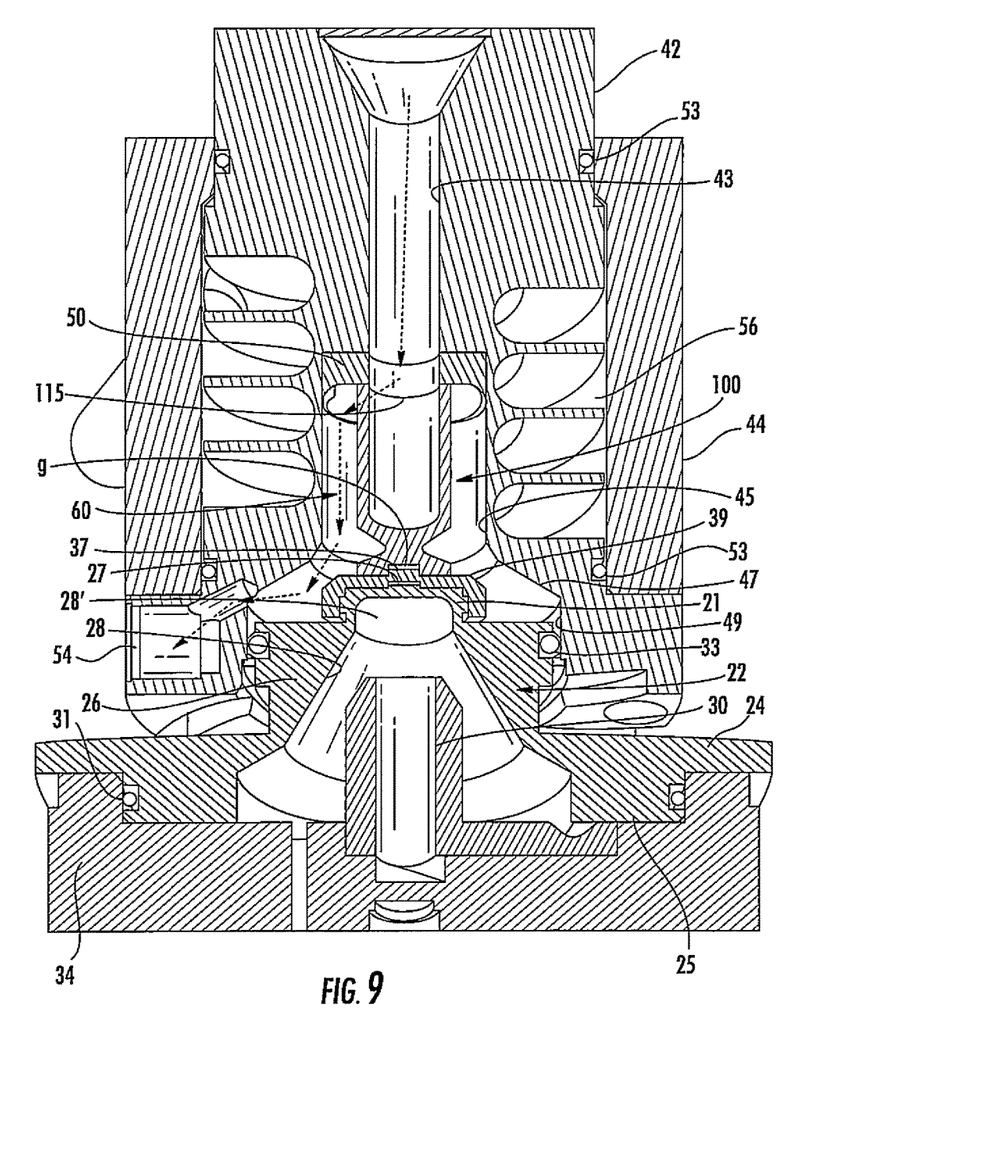
FIG. 9 is a pictorial cross-sectional view of the structure shown in FIG. 8, illustrating in dotted lines the inert gas flow path through the furnace.

O-ring seals 31 seal the electrode 22 within water cooling jacket 34, as illustrated in FIGS. 7-9, while O-rings 33 seal the pedestal 26 within the upper electrode assembly 40 when in a closed position, as also illustrated in these figures. The water jacket surrounding the lower electrode 22 includes a water inlet 32 coupled to nozzle 30, as seen in FIG. 8. The nozzle 30 includes a discharge opening 30' for directing cooling water, as shown by arrow "W" in FIG. 8, against the inside hollow undersurface of electrode 22. The water jacket 34 also includes an outlet 35 for discharging water from jacket 34. The flow path of the water which cools the inside of the volume of recess 28 of the lower electrode near the area of the tip 36 and projection 21 is shown in dotted lines in FIG. 8. The water can be recirculated through a cooler in a conventional manner.

The lower electrode assembly 20 sealably extends within the upper electrode assembly 40, as illustrated in FIGS. 7-9. For such purpose, the upper electrode assembly 40 likewise includes an electrode 42 surrounded by a cooling jacket 44 for receiving cooling water from a water inlet 46 (FIG. 8). Cooling water flows around spiral fins 48 extending radially outwardly from electrode 42 and is discharged through outlet 51. Upper and lower O-ring seals 53 seal water jacket 44 to the upper electrode 42, as seen in FIGS. 5 and 7-9. FIGS. 8 and 9 illustrate the preferred embodiment of the upper electrode fin construction, which provides enlarged water cooling channels 56 to significantly increase the flow rate of cooling water over the smaller channels shown in FIGS. 3, 5, and 7. The upper electrode water flow path is also illustrated by the dotted lines in FIG. 8.

Figure 10:
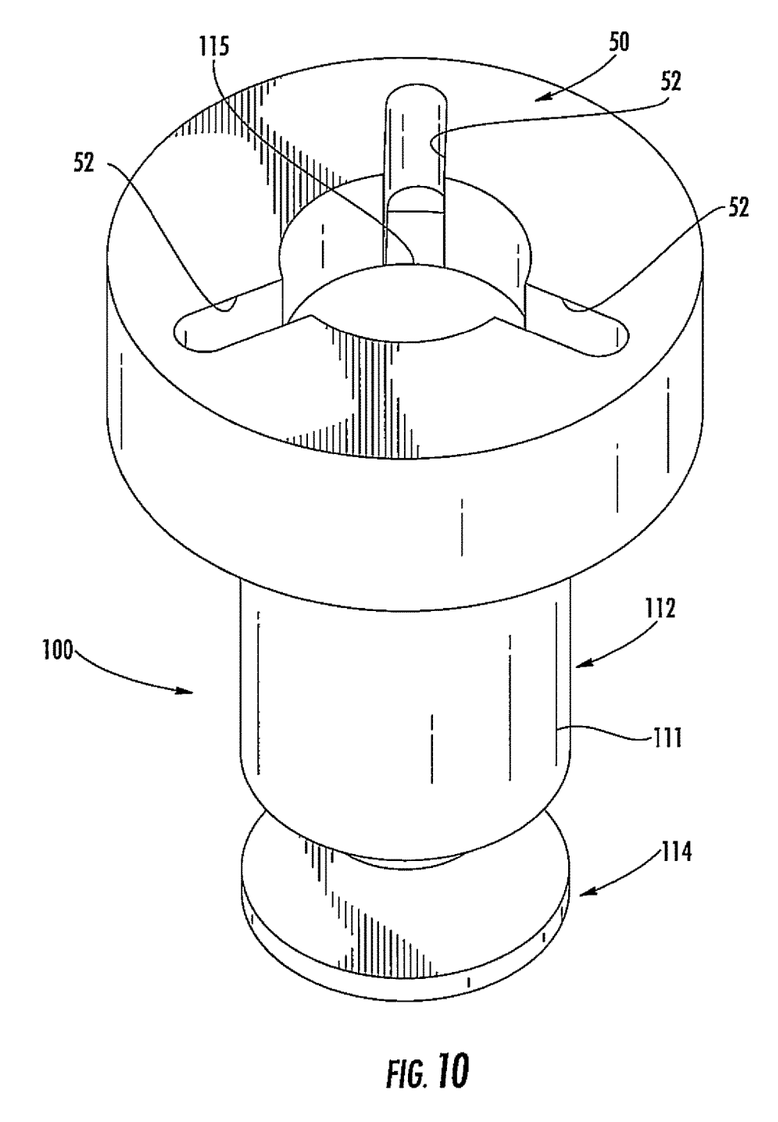
FIG. 10 is a fragmentary perspective view illustrating the relationship of the crucible and the tip member of the upper electrode shown also in FIGS. 7-9.

The upper electrode 42 includes an upper funnel-shaped opening 41 for receiving samples from a sample drop mechanism 62 (FIG. 2), which is mounted to the furnace 60 directly above the upper electrode 42. Mechanism 62 is described in U.S. Pat. No. 6,291,802, the disclosure of which is incorporated herein by reference. The upper electrode 42 includes an axially extending cylindrical aperture or tube 43 communicating with opening 41 and extending downwardly and terminating in an enlarged cylindrical opening 45 defining a furnace chamber 60 which receives the crucible 100 and lower electrode 22, as seen in FIGS. 7-9. The lower end of cylindrical opening 45 is beveled, enlarged, and outwardly tapered at wall 47 and has a cylindrical opening 49 for sealably receiving the lower electrode, as seen in FIGS. 7-9. The interface between tube 43 and the enlarged cylindrical opening 45 includes an annular tungsten carbide insert 50, which engages the annular upper rim 115 of crucible 100, as seen in FIGS. 8-10. The enlarged cylindrical opening 45 defines the furnace area 60, which receives the graphite crucible 100 during the fusion process when electrical power is applied to the electrodes 22 and 40. In order for the gaseous byproducts of fusion of a sample to escape the crucible 100, radially extending slots 52 (FIG. 10) are provided in the insert 50. This provides a gas flow path, as illustrated in dotted lines in FIG. 9, for the helium which is injected through the tube 43 to gather the analyte gases from the crucible during fusion of a sample and exit through outlet 54 of the electrode 42 to the analyzer detectors for detecting analytes of interest.

This improved electrode construction provides significantly better water cooling, such that the upper and lower electrodes operate at cooler temperatures, averaging from 500° C. to 600° C. as compared to the prior electrodes which operated at a temperature range of from about 800° C. to 900° C. with hot spots exceeding 1000° C. This results in a significantly longer electrode life as well as the life of the electrode tip 36 and insert 50. The improved cooling is partially responsible for this success as is the cooperation and synergistic relationship of the electrodes and tip with the design of crucible 100, which allows fusing of a specimen with lower power consumption. The crucible 100 is described in detail in conjunction with FIGS. 11-15.

Figure 11:
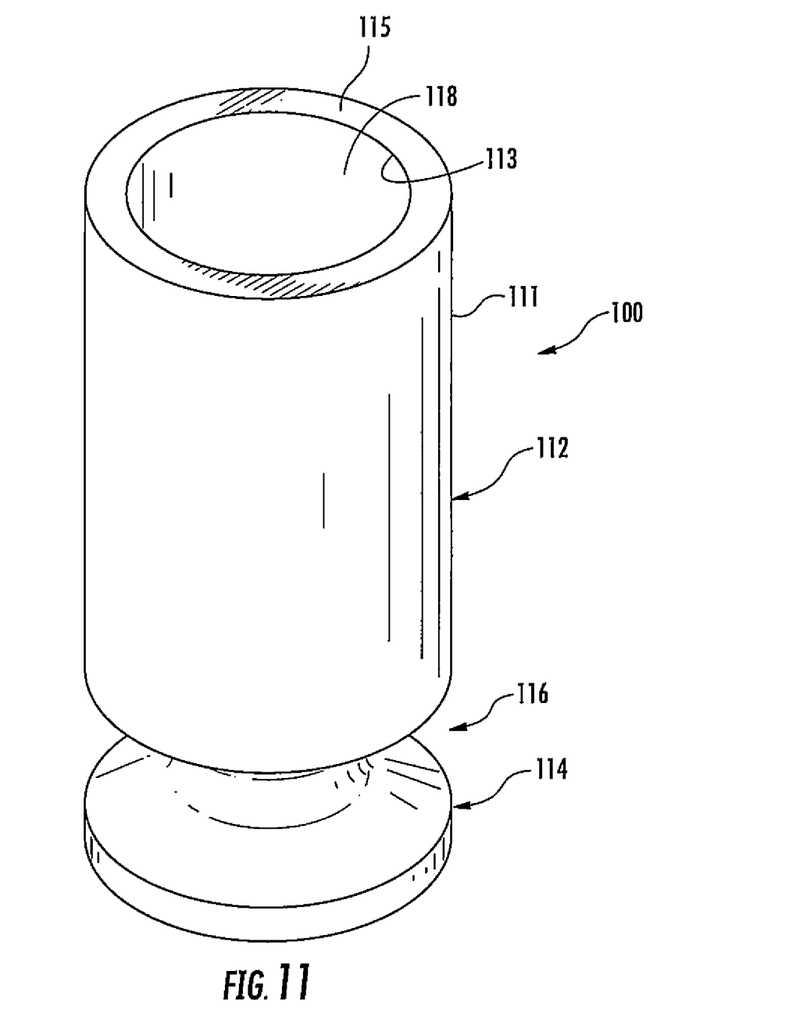
FIG. 11 is a perspective view of the crucible.
Figure 14:
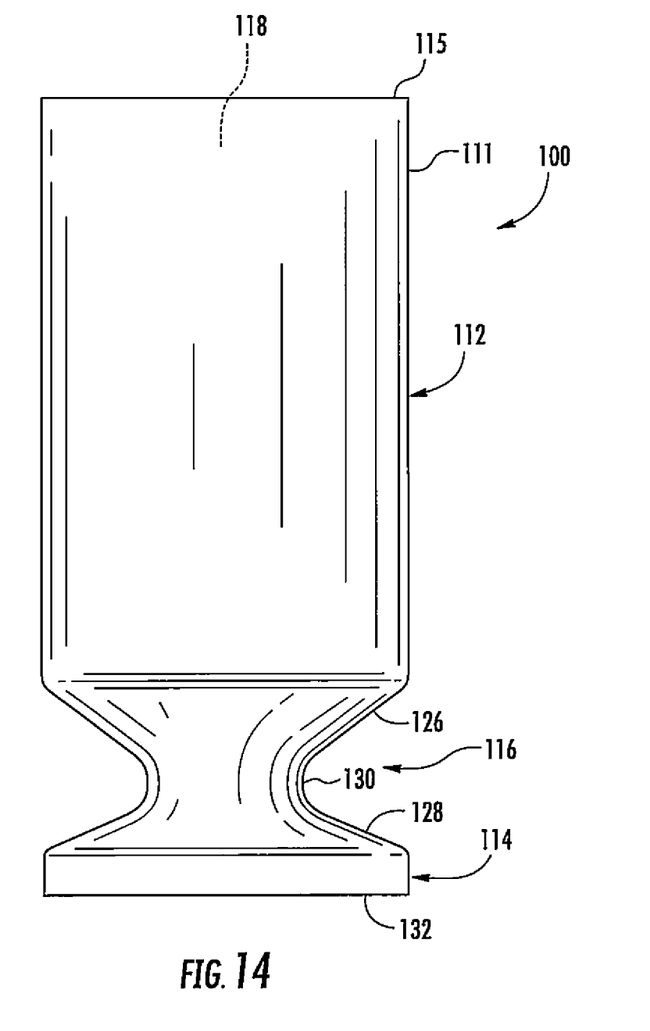
FIG. 14 is a side elevational view of the crucible.

Referring initially to FIGS. 11 and 14, there is shown a crucible 100 which cooperates with the furnace electrodes to provide the greatly improved performance of the present invention. Crucible 100 is made of commercial grade graphite and is machined from a solid graphite rod. The crucible has a cylindrical body 112, supported by a pedestal base 114 between which there is an annular inwardly extending concave indentation 116. The crucible has an open mouth 118 at the top for receiving specimens ranging from about 0.1 gram to 1 gram in size. The specimens can be in any form but typically are pins or chips which likewise are frequently encased in a nickel basket serving as an accelerator during the fusion process. The sample can be introduced manually in some systems or preferably by automation through tube 43 in the upper electrode assembly 40 and a sample drop mechanism as described in U.S. Pat. No. 6,291,802.

Figure 13:
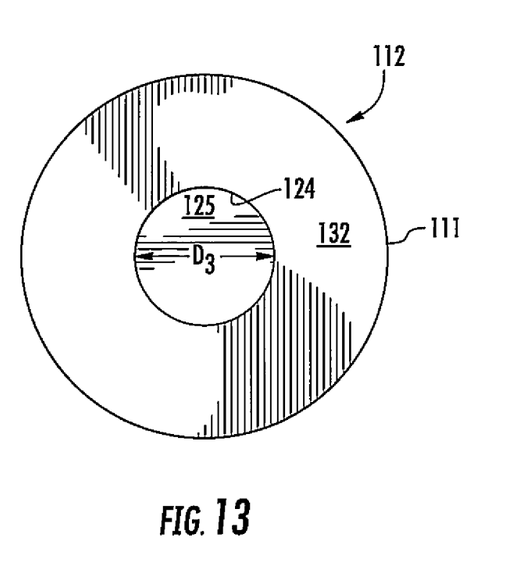
FIG. 13 is a bottom plan view of the crucible.
Figure 15:
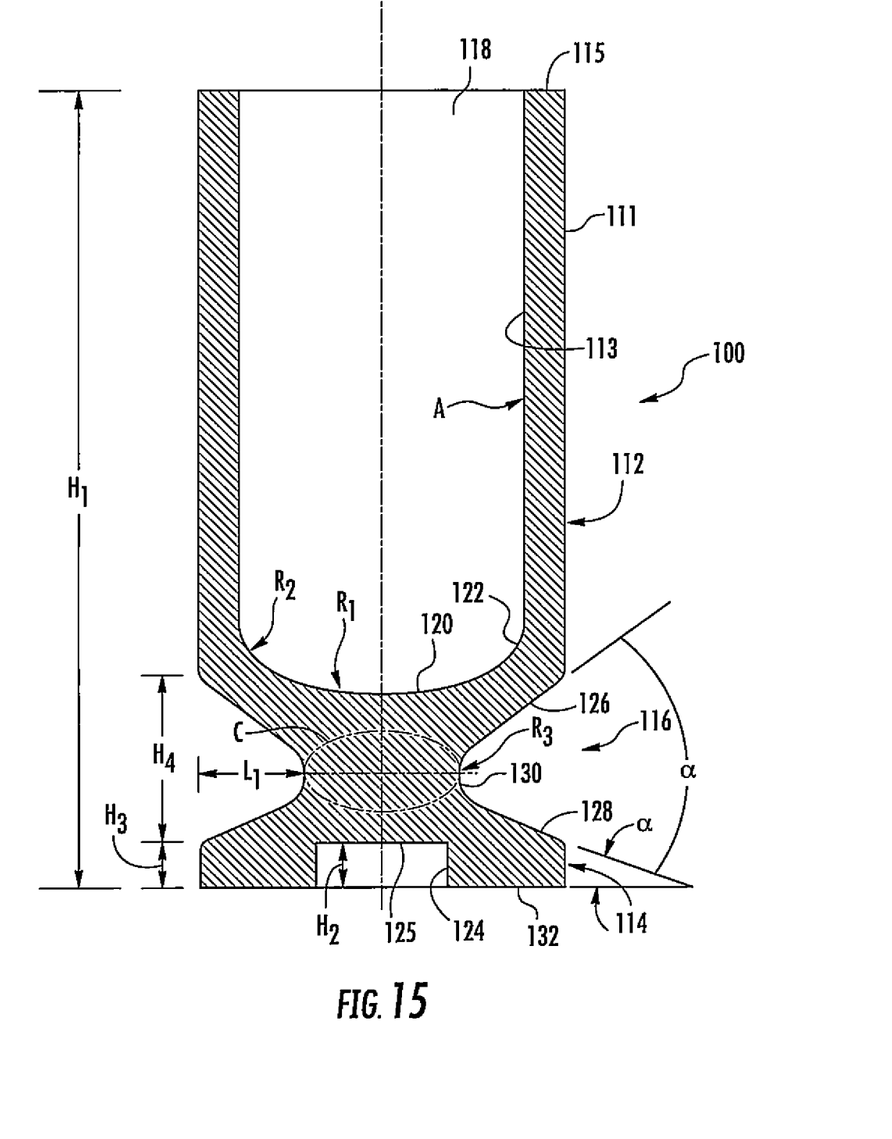
FIG. 15 is a vertical cross-sectional view of the crucible, taken along section lines XV-XV in FIG. 12.

The cylindrical body 112 includes an outer cylindrical wall 111 and an inner cylindrical wall 113. As seen in FIG. 15, the interior of the crucible also includes a floor 120 which is concavely curved at a first radius of curvature $R_1$. The floor communicates with the interior side wall 113 of the cylindrical body at a curved junction 122 having a second radius of curvature $R_2$. As seen in FIGS. 13 and 15, the pedestal base has a centrally located circular indentation 124. The annular indentation 116 includes an upper wall 126 and a lower wall 128, which converge at an apex 130 having a radius of curvature $R_3$. The smoothly curved, inwardly concave annular indentation 116 has the walls 126, 128 diverging outwardly from apex 130 at an angle α of 56° to 60°, as illustrated in FIG. 15. The angle β from the lower wall 28 to the floor is from 22°-24°.

The geometry of crucible 100, as best seen in FIG. 15, including the arcuate indentation 116 and circular indentation 124, results in a current choke zone circled and identified by the letter C in FIG. 15. With this design, the current flows from the annular bottom surface 132 of the pedestal, which engages the annular surface 39 of the tip 36 on projection 21 of lower electrode 22 of the furnace, as described above, through the choke zone C. The upper annular surface 115 of the crucible 100 engages the insert 50 of upper electrode 42 of the furnace, such that the current passes through the crucible between surfaces 132 and 115. The geometry of the crucible with the dimensions noted below resulted in a uniform heating of the floor 120 of the crucible and the side wall 113 through the zone between the floor 120 up to the area of arrow A in FIG. 15. Unexpectedly, this geometry allowed heating of a specimen positioned in a crucible at a much lower power than is typical.

Figure 12:
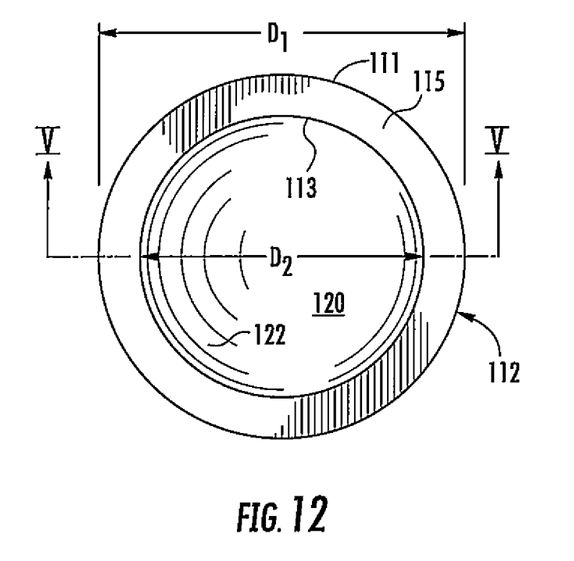
FIG. 12 is a top plan view of the crucible.

As noted above, in prior furnaces, the furnace power was approximately 7500 watts when a voltage of about 6.25 volts was supplied at a current of 1200 amps. With the present crucible 100, at the same 6.25 volts, only 800 amps of current is required providing a power of 5000 watts to achieve the same about 3000° C. fusion temperature within the crucible 100. This unexpected power savings of approximately 30% not only saves the laboratory using the furnace for analysis of specimens electricity costs but also allows the manufacture of the furnace to employ less expensive components since a lower current power supply can be used. The dimensions identified below and shown in FIGS. 12, 13, and 15 provided optimized performance for the preferred embodiment of the invention. Although these dimensions were optimized for the crucible, they may be varied somewhat. The depth, diverging angle, and radius of curvature of indentation 116, however, is of great importance.

The diameter $D_3$ (FIG. 13) of the indentation 124 in the pedestal was about 0.19 inches, with a depth $H_2$ (FIG. 15) of about 0.056 inches. The overall crucible height $H_1$ (FIG. 15) is 1.1 inches, while the height of pedestal base 114 $H_3$ (FIG. 15) was about 0.060 inches. The distance $H_4$ between the upper edge of the pedestal base 114 and the lower edge of the outer cylindrical body 112 of the crucible (i.e., the open mouth of the arcuate indentation 116) was about 0.224 inches. The radius of curvature $R_1$ of floor 120 was 0.35 inches while the junction of the floor 120 to the side wall 113 has a radius of curvature $R_2$ of 0.060 inches. The indentation 116 has diverging upper and lower side walls 126, 128 at an angle α of from about 56° to about 60°, and preferably about 58°. The angle β from the lower wall 28 to the floor is from 22°-24°. The radius of curvature $R_3$ of the smoothly curved annular indentation 116 is about 0.050 inches. The depth $L_1$ (FIG. 15) of indentation 116 is about 0.166 inches. The outer diameter $D_1$ (FIG. 12) of the crucible was 0.50 inches while the inner diameter $D_2$ was 0.39 inches, leaving a wall thickness of 0.055 inches.

It is expected that the specific dimensions given can vary within the normal manufacturing tolerances of machining of such crucibles and may be varied by as much as up to 3%, although it was discovered that the smoothly curved annular indentation 116 dimensions and geometry are critical to the successful functioning of the crucible to provide the unexpected uniform heating as well as lower power consumption. The crucible is subjected to approximately 83 pounds force when positioned between the upper and lower electrodes, as disclosed above. The maximum resistance area at the lower part of crucible 100 is the current choke area identified by arrow C in FIG. 15 and results in, together with the indentation 116, the uniform heating of the floor 120 of the crucible and the side walls up to the area of arrow B (FIG. 15). This provides improved uniform heating of specimens introduced into the crucible and prevents the fused specimen from bubbling over the top of the crucible through mouth 118 contaminating the upper electrode. The crucible height $H_1$ is slightly (10%) higher than the usual crucible construction, which also assists in the prevention of specimens reaching the insert 50 of the upper electrode 42.

It will become apparent to those skilled in the art that various modifications to the preferred embodiment of the invention as described herein can be made without departing from the spirit or scope of the invention as defined by the appended claims.

The invention claimed is:

1. An electrode assembly for a resistance analytical furnace comprising:
   a cylindrical upper electrode including a central axially extending aperture configured for admission of a sample into a crucible, an enlarged cylindrical area below said central axially extending aperture, and a funnel-shaped lower end configured to receive a pedestal of a lower electrode;

the lower electrode including said pedestal configured to support the crucible thereon; said pedestal shaped to be raised into sealable engagement within said funnel-shaped lower end of said upper electrode; said lower electrode including a bottom with an upwardly extending truncated conical recess, a cooling water inlet, and a cooling water outlet communicating with said truncated conical recess, wherein said pedestal of said lower electrode includes a center threaded projection which receives a threaded lower electrode tip, said threaded lower electrode tip which is generally cup-shaped with internal threads which threadably mate with said threaded projection on said lower electrode, wherein said threaded lower electrode tip comprises an alloy of tungsten and copper, and wherein said threaded lower electrode tip includes a centered circular upward projection shaped to extend within a circular recess in the bottom of the crucible;

a nozzle positioned in said lower electrode and coupled to said water inlet, said nozzle having an exit end spaced close to an inside surface of said truncated conical recess for projecting cooling water toward said pedestal of said lower electrode; and further including an upper electrode outer jacket surrounding said upper electrode, wherein said upper electrode includes cooling fins and said jacket surrounds said fins, said outer jacket including a cooling water inlet and a cooling water outlet for receiving water for cooling said upper electrode.

2. A cooling system for the electrodes of a resistance analytical furnace comprising:

upper and lower electrodes configured to hold a graphite crucible between them, said lower electrode including a bottom having a recess formed therein, wherein said lower electrode has a crucible-receiving pedestal and said recess has a truncated conical shape with a thin upper wall;

a water jacket surrounding said lower electrode, said jacket including a water inlet and a water outlet;

a nozzle positioned in said lower electrode and coupled to said water inlet which directs water toward said bottom of said lower electrode; and further including an upper water jacket surrounding said upper electrode, said upper water jacket including a water inlet and a water outlet, and wherein said upper electrode has a plurality of spiral fins extending radially outwardly into said upper water jacket.

3. The system as defined in claim 2, wherein said pedestal of said lower electrode includes a center threaded projection for receiving a threaded lower electrode tip.

4. The system as defined in claim 3, wherein said threaded lower electrode tip is generally cup-shaped with internal threads which threadably mate with said threaded projection on said lower electrode.

\* \* \* \* \*